United States Patent [19]
Grivsky

[11] Patent Number: 4,959,474
[45] Date of Patent: Sep. 25, 1990

[54] DIALKOXY PYRIDOPYRIMIDINE COMPOUNDS

[75] Inventor: Eugene M. Grivsky, Fairfax, Va.

[73] Assignee: Burroughs Wellcome Co., Research Triangle Park, N.C.

[21] Appl. No.: 786,725

[22] Filed: Oct. 15, 1985

Related U.S. Application Data

[63] Continuation of Ser. No. 381,365, May 24, 1982, abandoned, and a continuation of Ser. No. 159,246, Jun. 13, 1980, abandoned.

[30] Foreign Application Priority Data

Jun. 14, 1979 [GB] United Kingdom ............... 7920706

[51] Int. Cl.$^5$ .......................................... C07D 471/04
[52] U.S. Cl. ................................... 544/279; 544/323; 546/286; 546/289; 546/309; 546/310; 546/316; 546/322
[58] Field of Search ......................................... 544/279

[56] References Cited

U.S. PATENT DOCUMENTS

| | | | |
|---|---|---|---|
| 3,288,792 | 11/1966 | Hitchings et al. | 544/279 |
| 3,322,765 | 5/1967 | Hitchings et al. | 544/279 |

FOREIGN PATENT DOCUMENTS

| | | | |
|---|---|---|---|
| 709394 | 5/1965 | Canada | 544/279 |
| 913710 | 12/1962 | United Kingdom . | |
| 970583 | 9/1964 | United Kingdom | 544/279 |
| 1084103 | 9/1967 | United Kingdom . | |

*Primary Examiner*—Glennon H. Hollrah
*Assistant Examiner*—James H. Turnipseed
*Attorney, Agent, or Firm*—Donald Brown

[57] ABSTRACT

A novel class of 2,4-diamino-6-(2,5-dialkoxybenzyl)-5-methyl[2,3-d]-pyrimidines is described. These compounds are antibacterial agents, active against certain Streptococcus species. They are also active antiproliferative agents.

3 Claims, No Drawings

DIALKOXY PYRIDOPYRIMIDINE COMPOUNDS

This application is a continuation, of application Ser. No. 381,365, filed May 24, 1982 now abandoned and Ser. No. 159,246 filed on June 13, 1980 now abandoned.

The present invention relates to 2,4-diaminopyrido(2,3-d)pyrimidines, to pharmaceutical formulations comprising such compounds and to their use in medicine.

U.K. patent No. 1 084 103 discloses 2,4-diaminopyrido[2,3-d]pyrimidines of the general formula (I) in which $R^1$ is an alkyl group and $R^2$ is an unsubstituted benzyl group or a benzyl group substituted by one or more halogen atoms, alkyl or alkoxy groups.

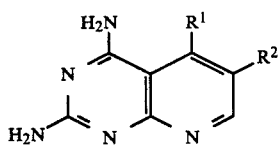

The compounds of formula (I) were described as having high in vitro and in vivo activity against bacteria or bacterial infections in experimental animals.

It has now been unexpectedly found that the compound 2,4-diamino-6-(2,5-dimethoxybenzyl)-5-methyl-pyrido[2,3-d]pyrimidine and pharmaceutically acceptable acid addition salts thereof are unexpectedly about 10-fold (900%) more active than the well known and highly potent antibacterial trimethoprim against *Streptococcus pyrogenes* and *Streptococcus faecalis*.

*Streptococcus faecalis* are of importance as penicillin resistant pathogens in diseases such as endocarditis and in genito-urinary and wound infections in humans and animals. *Streptococcus pyrogenes* is also known to cause bacterial infections in humans and animals.

The invention accordingly provides compounds of formula (II):

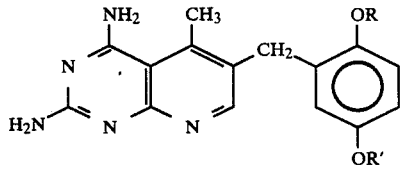

wherein R and R' are lower ($C_1$–$C_6$) alkyl and pharmaceutically acceptable acid addition salts thereof. Preferably monobasic salts are provided. Preferably R and R' are methyl.

The activity of the compound of formula (II) resides in the free base and thus the nature of the acid participating in the acid addition salts is of minor importance. Such acid addition salts include, for example, those derived from hydrochloric acid, hydroiodic acid, sulphuric acid, phosphoric acid, acetic acid, p-toluenesulphonic acid, methanesulphonic acid, maleic acid, lactic acid, citric acid, tartaric acid, succinic acid, oxalic acid, p-chlorobenzenesulphonic acid, glucuronic acid, pantothenic acid and lactobionic acid.

The compound of formula (II) may be prepared by any method known in the art for the preparation of compounds of analogous structure.

In particular the compound of formula (II) may be prepared by the reductive cleavage of the corresponding 7-substituted compound of formula (III):

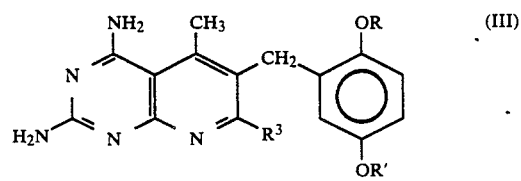

wherein R and R' are as defined above and $R^3$ is a leaving group capable of being removed by hydrogenolysis. Such groups include for example a mercapto or halogeno (e.g. chloro) group.

Where in the compound of formula (III) $R^3$ is SH the dithiation may for instance be conveniently effected by reaction with a reducing agent, for example Raney nickel or Raney cobalt or by catalytic hydrogenation utilizing hydrogen in the presence of a catalyst such as palladium on charcoal.

The compound of formula (III) wherein $R^3$ is a mercapto group may be prepared from the corresponding 7-chloro compound [(III), $R^3$=Cl] by reaction with a hydrosulfide as described in U.K. patent No. 913 710 or by treatment of the corresponding 7-hydroxy compound with phosphorus pentasulfide.

In the case where $R^3$ is a halogen atom, the compound of formula (III) the compound of formula (II) may for instance be conveniently obtained by e.g. catalytic hydrogenation.

The compound of formula (II) may also be prepared by reacting 2,4,6-triamino pyrimidine (IV) with a compound of formula (V):

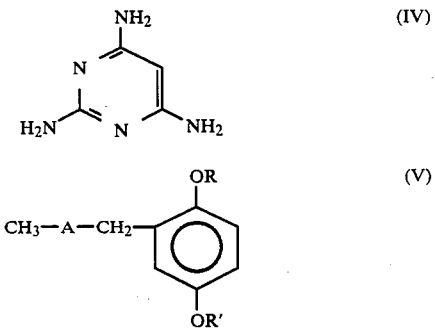

wherein A is selected from

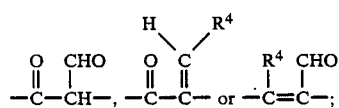

R and R' are as defined above; and $R^4$ is a leaving group such as for example a tertiary amino, alkoxy, alkylthio, halo, sulphonate or tosylate group.

The compound of formula (II) may additionally be prepared by the conversion to amino groups, by methods known in themselves in pyrimidine chemistry, of the hydroxy and/or mercapto groups(s) in the compound of formula (VI):

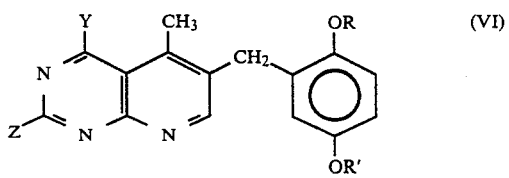

in which R and R' are as defined above and Y and Z are the same or different and are OH, SH or $NH_2$ provided that at least one of Y and Z is OH or SH.

Compounds of formula (VII) may be prepared by methods known in the art for the preparation of such compounds. In addition, those in which Y is OH or $NH_2$ and Z is OH or SH may be obtained, for example, by reaction of urea, guanidine or thiourea with a suitable compound of formula (VII):

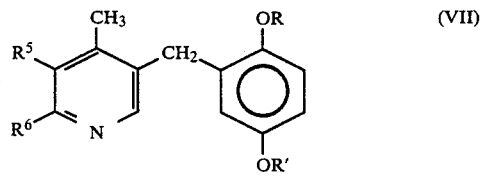

in which R and R' are as defined above and $R^5$ is —$CO_2H$, $CO_2$Alkyl, $CONH_2$ or CN; and $R^6$ is $NH_2$, Cl or Br.

While it is possible for the compound of formula (II) or an acid addition salt thereof (hereinafter referred to as the "active compounds") to be administered as the raw chemical it is prefereably presented in the form of a pharmaceutical formulation.

The invention therefore further provides a pharmaceutical formulation comprising the active compound together with a pharmaceutically acceptable carrier therefor. The carrier must be "acceptable" in the sense of being compatible with the other ingredients of the formulation and not deleterious to the recipient thereof.

The invention additionally provides a method for the preparation of a pharmaceutical formulation comprising bringing into association an active compound and a pharmaceutically acceptable carrier therefor.

Topical application is particularly suitable when the active compounds are for use in the treatment of bacterial skin diseases, caused by the bacteria previously mentioned.

The term "topical" as applied herein relates to the use of the active ingredient incorporated in a suitable pharmaceutical carrier, and applied at the site of the disease for the exertion of local action.

Pharmaceutical formulations suitable for topical administration may be presented in anhydrous forms such as ointments, lotions, pastes, jellies, sprays, aerosols, and bath oils. The term ointment includes formulations (including creams) having oleaginous, absorption, water-soluble and emulsion type bases, for example petrolatum, lanolin, polyethylene glycols and mixtures thereof.

Topical formulations may contain a concentration of the active ingredient of from about 0.05 to about 2% w/w, preferably about 0.1 to about 1% w/w, most preferably about 0.2 to about 0.5% w/w.

Other pharmaceutical formulations include those suitable for oral, rectal, and parenteral administration although of these oral is preferred. The formulations may, where appropriate, be conveniently presented in discrete dosage units and may be prepared by any of the methods well known in the art of pharmacy. A convenient unit dose formulation for the aforementioned bacterial infections contains the active compound in an amount of from about 50 mg to about 2 g, preferably about 100 mg to about 500 mg, most preferably about 200 mg, to be taken once or several times daily.

All methods for the preparation of such formulations include the step of bringing into association the active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules, cachets or tablets each containing a predetermined amount of the active compound. A tablet may be made by compression or moulding, optionally with one or more accessory ingredients. Compressed tablets may be prepared by compressing in a suitable machine the active compound of formula (II) in a free-flowing form such as a powder or granules optionally mixed with a binder, lubricant, inert diluent, lubricating, surface active or dispersing agent. Moulded tablets may be made by moulding an inert liquid diluent. Tablets may be optionally coated and, if uncoated, may be optionally scored. Capsules may be prepared by filling the active compound either alone or in admixture with one or more accessory ingredients, into the capsule cases and then sealing them in the usual manner. Cachets are analogous to capsules wherein the active ingredient together with any accessary ingredient(s) is sealed in a rice paper envelope.

Pharmaceutical formulations suitable for oral administration wherein the carrier is a liquid may be presented as a solution or a suspension in an aqueous liquid or as an oil-in-water or water-in-oil liquid emulsion.

Pharmaceutical formulations suitable for rectal administration wherein the carrier is a solid are most preferably presented as unit dose suppositories. Suitable carriers include cocoa butter and other material commonly used in the art, and the suppositories may be conveniently formed by admixture of the active compound with the softened or melted carrier(s) followed by chilling and shaping in moulds.

Pharmaceutical formulations suitable for parenteral administration include sterile solutions or suspensions of the active compound in aqueous or oleaginous vehicles. Such preparations are conveniently presented in unit dose or multi-dose containers which are sealed after introduction of the formulation until required for use.

It should be understood that in addition to the aforementioned carrier ingredients the pharmaceutical formulations described above may include, as appropriate, one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended reipient.

As has been described above the compounds of the present invention are particularly useful for the treatment of bacterial infections caused by the aforementioned bacteria. The invention thus further provides a method for the treatment of bacterial infections in mammals by the aforementioned bacteria which comprises the administration of an effective, non-toxic amount of the compound of formula (II) or an acid addition salt thereof once or several times a day orally or applied topically.

The treatment of *Streptococcus faecalis* and *Streptococcus pyrogenes* bacterial infections in animals is preferably accomplished by the oral or parenteral administration of pharmaceutical formulations containing the compound of formula (II) or pharmaceutically acceptable salt thereof. Oral administration is preferred. For treatment of bacterial infections caused by *Streptococcus faecalis* and *Streptococcus pyrogenes* administration of about 1-10 mg/kg of body weight, preferably about 4-10 mg/kg per day should be given in 3 or 4 divided doses. The compound of formula (II) may also be administered together with sulfonamides, in which case the preferred range is about 1-5 mg/kg/day in 3 or 4 divided doses.

Toxic manifestations attributable to the active compound are typically those associated with folate depletion, such as bone marrow depression, megaloblastic changes, and gastrointestinal ulceration. Calcium leucovorin (calcium salt of 5-formyl-5,6,7,8-tetrahydrofolic acid) may be administered to effect reversal of these toxic manifestations or to prevent their occurrence. The administration of calcium leucovorin may be effected concurrently with treatment or at any stage thereof whenever toxic symptoms appear.

Thus, the haematological activity of the active compound can be prevented or reduced by the simultaneous administration of leucovorin. Consequently, tissue levels of the compound may be safely raised by increasing the dose of the compound together with a simultaneous administration of leucovorin.

EXAMPLE 1

2,4-Diamino-6-(2,5-dimethoxybenzyl)-5-methylpyrido[2,3-d]pyrimidine

A mixture of 2,5-dimethoxybenzaldehyde (100 g), ethyl acetoacetate (84.5 g) and anhydrous benzene (200 ml), piperidine (6 ml) and acetic acid (12 ml) was heated at reflux for 3 hours in an apparatus fitted with a Dean-Stark trap to collect the azeotropically distilled water. The reaction mixture was cooled, benzene (300 ml) added, and the solution was washed successively with water (100 ml), cold 0.1N hydrochloric acid (200 ml), 5% aqueous sodium bicarbonate (200 ml) and dilute acetic acid (100 ml) and dried over anhydrous magnesium sulfate. The solvent was then removed under reduced pressure and the residual oil distilled, b.p. 169°-170° C./0.3 mm Hg. The product, ethyl α-(2,5-dimethoxybenzylidene)acetoacetate, solidified on standing (104 g, m.p. 68°-69° C.) and was recrystallized from ethanol-pentane (m.p. 72°-73° C.). A portion (38 g) of the product was reduced catalytically in the presence of palladium on charcoal catalyst (Pd/C) in ethyl acetate (150 ml). The product, after removal of solvent, was purified by distillation under reduced pressure to give ethyl α-(2,5-dimethoxybenzyl)acetoacetate, b.p. 146°-148° C./0.3 mm Hg.

A mixture of ethyl α-(2,5-dimethoxybenzyl)acetoacetate (21.2 g), 2,4,6-triaminopyrimidine (10 g) and diphenyl ether (100 ml) was heated at 190°-230° C. for 1.5 hours in an apparatus fitted with a Dean-Stark trap and water-ethanol (4 ml) was collected. Methanol (200 ml) and ethanol (50 ml) was added to the cooled reaction mixture. The resulting solid was collected by filtration and treated with boiling water (1 l) to give 2,4-diamino-5-methyl-6-(2,5-dimethoxybenzyl)-7-oxo-7,8-dihydropyrido[2,3-d]pyrimidine (17 g), m.p. 325°-326° C.

2,4-Diamino-5-methyl-6-(2,5-dimethoxybenzyl)-7-oxo-7,8-dihydropyrido[2,3-d]pyrimidine (8 g) was chlorinated by treatment with Vilsmeier reagent prepared by slowly adding thionyl chloride (28.6) in dry chloroform (25 ml) to a solution of dimethylformamide (17.5) in chloroform (100 ml) at 0°-5° C. The cold mixture of the pyridopyrimidine and Vilsmeier reagent was stirred, gradually allowed to reach ambient temperatures and then heated at reflux for 3 hours. It was then treated with ethanolic base (80 ml) maintaining the temperature at 25°-30° C. with cooling. The brown product formed was isolated, treated further with aqueous ammonia and then recrystallized from ethanol to give 2,4-diamino-5-methyl-6-(2,5-dimethoxybenzyl)-7-chloropyrido[2,3-d]pyrimidine, m.p. 193°-196° (dec.).

The chloro compound (0.3 g) was dissolved in ethanol (200 ml) containing potassium hydroxide (0.2 g). Palladium on charcoal catalyst (0.2 g) was added and hydrogenation commenced. Reduction was complete after 48 hours and yielded 2,4-diamino-5-methyl-6-(2,5-dimethoxybenzyl)pyrido[2,3-d]pyrimidine, m.p. 252°-254° C.

EXAMPLE 2

Tablet Formulation

|  | amount |
|---|---|
| 2,4-Diamino-5-methyl-6-(2,5-dimethoxybenzyl)-pyrido[2,3-d]pyrimidine | 100 mg |
| Starch | 50 mg |
| Lactose | 50 mg |
| Stearic acid | 3 mg |
| Gelatin | 15 mg |
| TOTAL | 218 mg |

EXAMPLE 3

Water Soluble Ointment

|  | amount (g) |
|---|---|
| 2,4-Diamino-6-(2,5-dimethoxybenzyl)-5-methylpyrido[2,3-d]-pyrimidine | 0.5 |
| Polyethylene glycol 300 | 20.0 |
| Polyethylene glycol 1500 | 79.5 |
| Total | 100.0 |

EXAMPLE 4

Skin Cream

|  | amount (g) |
|---|---|
| 2,4-Diamino-6-(2,5-dimethoxybenzyl)-5-methylpyrido[2,3-d]-pyrimidine | 0.5 |
| Glyceryl monostearate | 20.0 |
| Methylparaben | 0.3 |
| Petrolatum, light liquid | 4.0 |
| Propylene glycol | 5.0 |
| Span 60 | 2.0 |
| Tween 61 | 4.0 |
| Water | 64.2 |
| Total | 100.0 |

EXAMPLE 5

Injectable

| | amount |
|---|---|
| 2,4-Diamino-6-(2,5-dimethoxybenzyl)-5-methylpyrido[2,3-d]-pyrimidine | qs to 5 mg/ml |
| Propylene glycol | 40 ml |
| Ethanol | 11 ml |
| Water | 9 ml |

It was later discovered by others whose rights are assignable to Burroughs Wellcome Co. that the compounds of formula (II) have antiproliferative activity in mammals at doses of about 0.1 to about 100 mg/kg bodyweight per day when given orally or by injection, and when administered topically at concentrations of from about 0.05 to about 2% w/w. Among the proliferative diseases which compounds of formula (II) are useful in treating are: psoriasis, basal and squamous cell carcinomas of the skin and various forms of cancer including leukemias, lymphomas, sarcomas and solid tumors.

I claim:

1. 2,4-Diamino-6-(2,5-dimethoxybenzyl)-5-methyl-pyrido[2,3-d]pyrimidine.

2. A pharmaceutically acceptable acid addition salt of 2,4-Diamino-6-(2,5-dimethoxybenzyl)-5-methyl-pyrido[2,3-d]pyrimidine.

3. The hydrochloride salt of 2,4-diamino-6-(2,5-dimethoxybenzyl)-5-methypyrido[2,3-d]pyrimidine.

* * * * *